United States Patent
He et al.

(10) Patent No.: US 10,234,470 B2
(45) Date of Patent: Mar. 19, 2019

(54) ENZYME-LINKED IMMUNOSORBENT ASSAY KIT FOR DETECTING DINITOLMIDE AND USE THEREOF

(75) Inventors: Fangyang He, Beijing (CN); Yuping Wan, Beijing (CN); Caiwei Feng, Beijing (CN); Xiaoqin Luo, Beijing (CN); Jing Feng, Bejing (CN); Haifeng Cui, Beijing (CN); Nianqin Xu, Beijing (CN); Liangliang Zhu, Beijing (CN); Yumei Liu, Beijing (CN); Fangfang Jia, Beijing (CN); Zhengmiao Zhao, Beijing (CN)

(73) Assignee: Beijing Kwinbon Biotechnology Co., Ltd., Beijing (CN)

( * ) Notice: Subject to any disclaimer, the term of this patent is extended or adjusted under 35 U.S.C. 154(b) by 952 days.

(21) Appl. No.: 14/412,317

(22) PCT Filed: Jul. 4, 2012

(86) PCT No.: PCT/CN2012/078164
§ 371 (c)(1),
(2), (4) Date: Apr. 15, 2015

(87) PCT Pub. No.: WO2014/005298
PCT Pub. Date: Jan. 9, 2014

(65) Prior Publication Data
US 2015/0219678 A1    Aug. 6, 2015

(51) Int. Cl.
*G01N 33/94* (2006.01)
*G01N 33/577* (2006.01)

(52) U.S. Cl.
CPC .......... *G01N 33/94* (2013.01); *G01N 33/577* (2013.01); *G01N 2430/00* (2013.01)

(58) Field of Classification Search
None
See application file for complete search history.

(56) References Cited

U.S. PATENT DOCUMENTS 3,627,883 A * 12/1971 Gorman ............... A23K 20/195
424/122

FOREIGN PATENT DOCUMENTS

CN       1837771 A      9/2006

OTHER PUBLICATIONS

He et al., "Application of the Enzyme-Linked Immune Technology in Food Safety and Drug Residue," *Modern Agricultural Sciences and Technology* 15:353-354, 2009. (3 pages) (with English Abstract).

* cited by examiner

*Primary Examiner* — Tracy Vivlemore
*Assistant Examiner* — Nam P Nguyen
(74) *Attorney, Agent, or Firm* — Seed IP Law Group LLP

(57) ABSTRACT

The present invention discloses an enzyme-linked immunosorbent assay kit for detecting dinitolmide and use thereof. The enzyme-linked immunosorbent assay kit of the present invention comprises dinitolmide antibody and coating antigen and enzyme conjugate; wherein, the dinitolmide antibody is dinitolmide monoclonal antibody or dinitolmide polyclonal antibody; when the coating antigen is the conjugate of dinitolmide hapten and carrier protein, the enzyme conjugate is enzyme-labeled secondary antibody, or enzyme-labeled specific anti-dinitolmide monoclonal or polyclonal antibody; when the coating antigen is dinitolmide antibody or secondary antibody, the enzyme conjugate is enzyme-labeled dinitolmide hapten. The enzyme-linked immunosorbent assay kit has a simple structure, and it is convenient for use, cheap and portable. Its detection is high effective, accurate, and convenient. It can be used for on-site monitoring and is suitable for qualitative and quantitative screenings of a great number of samples. And thus, it will play an important role in the detection of dinitolmide.

18 Claims, 2 Drawing Sheets

ENZYME-LINKED IMMUNOSORBENT ASSAY KIT FOR DETECTING DINITOLMIDE AND USE THEREOF

TECHNICAL FIELD

The present invention relates to an enzyme-linked immunosorbent assay technique. More particularly, the invention relates to an enzyme-linked immunosorbent assay kit for detecting dinitolmide and use thereof.

BACKGROUND

Dinitolmide is a nitrobenzamide coccidiostat developed by Dow Company (France) in 1960. It was approved for production and use in China in 1989. Dinitolmide is widely used due to its good efficacy for preventing and treating coccidium. However, during its application, if it is administrated with an overdose or continued to administrate in laying hens and during withdrawal time, there will be drug residues in animal products, and thus, some potential harms will be caused to human health. The Public Report No. 235 issued by the Ministry of Agriculture of China prescribes the maximum residual limit of dinitolmide is 3000 μg/kg in chicken and 6000 μg/kg in chicken liver, respectively. At present, however, there is no corresponding standard method of analyzing the residual analyst. So, it is necessary to carry out the study on the analysis method of measuring the residual amount of dinitolmide.

At present, the method of analyzing the residual amount of dinitolmide in animal feed and animal tissues mainly includes the thin layer chromatography, spectrophotometry and high performance liquid chromatography. Because of the complicated instruments, cumbersome process, high cost of detection and the high requirements for the skills of the technicians, these existing methods are not suitable for on-site monitoring and the screenings of a large number of samples.

DETAILED DESCRIPTION OF INVENTION

An objective of the invention is to provide an enzyme-linked immunosorbent assay kit for detecting dinitolmide.

The present invention provides an enzyme-linked immunosorbent assay kit for detecting dinitolmide, comprising: dinitolmide antibody, coating antigen and enzyme conjugate; wherein, the dinitolmide antibody is preferably dinitolmide monoclonal antibody or dinitolmide polyclonal antibody, preferably the coating antigen is the conjugate of dinitolmide hapten and carrier protein, or dinitolmide antibody or secondary antibody, and, preferably, the enzyme conjugate is enzyme-labeled goat anti-mouse secondary antibody or goat anti-rabbit secondary antibody, enzyme-labeled specific anti-dinitolmide monoclonal or polyclonal antibody or enzyme-labeled dinitolmide hapten.

When the coating antigen is the conjugate of dinitolmide hapten and carrier protein, the enzyme conjugate is enzyme-labeled goat anti-mouse secondary antibody or goat anti-rabbit secondary antibody, or enzyme-labeled specific anti-dinitolmide monoclonal or polyclonal antibody; and when the coating antigen is dinitolmide antibody or secondary antibody, the enzyme conjugate is enzyme-labeled dinitolmide hapten.

The carrier protein used in the present invention is any protein which is capable of forming an immunogen upon coupling with dinitolmide hapten, and is preferably selected from thyroid protein, bovine serum protein, mouse serum protein, rabbit serum protein, human serum protein, hemocyanin, fibrinogen or ovalbumin.

For the purpose of facilitating the on-site monitoring and the screenings of a large number of samples, the kit may further comprise dinitolmide standard solution series, substrate solution, concentrated washing solution, stop solution and/or concentrated extraction solution.

The concentrated washing solution may be 0.2 to 0.4 mol/L phosphate buffer comprising 0.2 to 1.0 wt % Tween-20 and 0.01 to 0.06 wt % sodium azide, pH 7.1-7.6; and the concentrated extraction solution may be 0.1 to 0.2 mol/L phosphate buffer, pH 7.2-7.8.

The substrate solution consists of substrate solution A and substrate solution B, wherein the substrate solution A may be hydrogen peroxide or urea hydrogen peroxide, and the substrate solution B may be o-phenylene diamine or tetramethyl benzidine. The stop solution may be 0.5 to 2 mol/L sulfuric acid or hydrochloric acid solution.

An amount of Tween-20 and sodium azide may be added to the washing solution because Tween-20 in the buffer not only reduces the non-specific adsorption of antibodies, but also has a certain protective effect on the proteins; and after the addition of sodium azide, it inhibits bacterial growth in the solution, and has a protective effect on the stability of the solution.

The dinitolmide hapten may be prepared as follows: catalytically (e.g., Pd/C) hydrogenating dinitolmide to produce a mono-amine derivative, and then reacting with succinic anhydride to produce the dinitolmide hapten (i.e., 5-amino nitolmide mono-succinamide).

The dinitolmide antibody is prepared by using the conjugate of the dinitolmide hapten and carrier protein as immunogen. Said carrier protein is selected from thyroid protein, bovine serum protein, mouse serum protein, rabbit serum protein, human serum protein, hemocyanin, fibrinogen or ovalbumin.

Dinitolmide is a small molecule, only has immune reactivity and no immunogenicity, so, it cannot induce an immune response in body, and it has to be coupled to a macromolecular carrier protein to gain the immunogenicity. In the present invention, the dinitolmide hapten is conjugated to carrier protein via carbodiimide method, so as to highlight the characteristic structure of dinitolmide and improve the immunogenicity and specificity of the dinitolmide hapten at the same time.

The dinitolmide monoclonal and/or polyclonal antibody may be a mouse-, horse-, goat-, rabbit- or guinea pig-derived antibody.

Preferably, the dinitolmide monoclonal antibody is an antibody secreted by dinitolmide monoclonal hybridoma cell line E-2-4 under the accession number of CGMCC No. 6143.

The enzyme-labeled secondary antibody is prepared by conjugating a conjugate enzyme to said secondary antibody via sodium periodate method. In the sodium periodate method, the ratio of the molar concentration of said conjugate enzyme to that of the secondary antibody is 2:1, and the conjugate enzyme is alkaline phosphatase or horseradish peroxidase, wherein horseradish peroxidase is preferred. In this modified sodium periodate method, the step of blocking the amino groups on the enzyme is omitted, thereby saving time, reducing the concentration ratio of horseradish peroxidase (HRP) to the secondary antibody, and saving the raw material.

Another objective of the present invention is to provide a method for detecting dinitolmide.

The present invention provides a method for detecting dinitolmide, comprising the following steps:

1) sample preparation: a homogeneous specimen of a sample is weighed and added to a centrifuge tube, and centrifuged after extracting with acetonitrile; the supernatant is removed and blow-dried in a water bath; the residue is dissolved by adding n-hexane, and the impurity is removed; the solution is extracted with extraction solution, and the bottom solution after centrifugation is used for analysis, wherein said sample is animal feed or animal tissue specimen, preferably is chicken feed, chicken meat or chicken liver;

2) quantitatively and/or qualitatively measuring said bottom solution of step 1) using any one of the enzyme-linked immunosorbent assay kit as described above; and optionally 3) analyzing the measurement results.

The murine monoclonal hybridoma cell line E-2-4 under the accession number of CGMCC No. 6143 is also within the protection scope of the present invention.

The enzyme-linked immunosorbent assay kit for detecting dinitolmide of the present invention quantitatively or qualitatively measures the residual amount of dinitolmide in a sample, mainly based on an ELISA method. As for this kit, the requirements for the preparation of sample is low, the process of the preparation of sample is simple, so that a large number of samples can be measured rapidly and simultaneously. The main agents in the kit are provided as working solutions. The detecting method is simple and easy to perform, and it has the property of high specificity, high sensitivity, high precision and high accuracy, and the like. The enzyme-linked immunosorbent assay kit of the present invention has a simple structure, and it is convenient for use, cheap and portable. Its detection is high effective, accurate, and simple. It can be used for on-site monitoring and is suitable for qualitative and quantitative screenings of a great number of samples. Thus, the kit of the invention will play an important role in the detection of dinitolmide.

EMBODIMENTS FOR CARRYING OUT THE INVENTION

Figure 1:
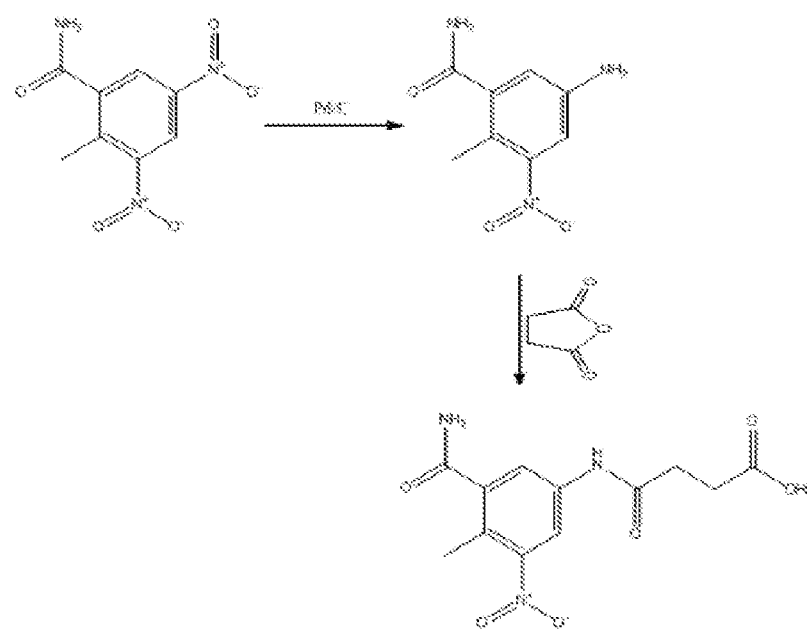
FIG. 1 is the schematic diagram of the synthesis of dinitolmide hapten.

The experimental methods used in the following Examples are conventional methods, unless indicated otherwise. And the chemical solvents used in the following Examples are commercially available solvents which are chemically pure, unless indicated otherwise.

Example 1 Kit Comprising the Conjugate of Dinitolmide Hapten and Carrier Protein as the Coating Antigen and the Detection Method Thereof I. An Enzyme-Linked Immunosorbent Assay Kit Comprising the Conjugate of Dinitolmide Hapten and Carrier Protein as the Coating Antigen Generally Comprises:

(1) a microtiter plate coated with the coating antigen (the coating antigen is the conjugate of dinitolmide hapten and carrier protein);

(2) enzyme-labeled secondary antibody working solution: horseradish peroxidase labeled goat anti-mouse secondary antibody or horseradish peroxidase labeled goat anti-rabbit secondary antibody;

(3) dinitolmide monoclonal antibody working solution or dinitolmide polyclonal antibody working solution;

(4) dinitolmide standard solution series (Shanghai Anpu Scientific Instrument Co., Ltd., Cat. No.: 148-01-6): six vials of solution having a concentration of 0 μg/L, 1 μg/L, 3 μg/L, 9 μg/L, 27 μg/L, and 81 μg/L, respectively;

(5) substrate solution which consists of substrate solution A and substrate solution B, wherein the substrate solution A is urea hydrogen peroxide or hydrogen peroxide, and the substrate solution B is tetramethyl benzidine or o-phenylene diamine;

(6) stop solution, which is 0.5 to 2 mol/L hydrochloric acid or sulfuric acid;

(7) concentrated washing solution, which is 0.2 to 0.4 mol/L phosphate buffer comprising 0.2 to 1.0 wt % Tween-20 and 0.01 to 0.06 wt % sodium azide, pH 7.1-7.6; and (8) a concentrated extraction solution, which is 0.1 to 0.2 mol/L phosphate buffer, pH 7.2-7.8.

II. An Enzyme-Linked Immunosorbent Assay Kit Comprising the Conjugate of Dinitolmide Hapten and Carrier Protein as the Coating Antigen Specifically Comprises:

(1) a microtiter plate coated with the coating antigen (the coating antigen is the conjugate of dinitolmide hapten and carrier protein);

(2) enzyme-labeled secondary antibody working solution: horseradish peroxidase labeled goat anti-mouse secondary antibody;

(3) dinitolmide monoclonal antibody working solution;

(4) dinitolmide standard solution series: six vials of solution having a concentration of 0 μg/L, 1 μg/L, 3 μg/L, 9 μg/L, 27 m/L, and 81 μg/L, respectively;

(5) a substrate solution which consists of substrate solution A and substrate solution B, wherein the substrate solution A is urea hydrogen peroxide, and the substrate solution B is tetramethyl benzidine;

(6) stop solution, which is 0.5 to 2 mol/L sulfuric acid;

(7) concentrated washing solution, which is 0.2 to 0.4 mol/L phosphate buffer comprising 0.2 to 1.0 wt % Tween-20 and 0.01 to 0.06 wt % sodium azide, pH 7.1-7.6; and (8) a concentrated extraction solution, which is 0.1 to 0.2 mol/L phosphate buffer, pH 7.2-7.8.

III. The Preparation of the Components of the Kit

1. The Synthesis of the Antigen a. The Synthesis of the Hapten (See FIG. 1)

Specifically, the steps for synthesizing the hapten are as follows:

Weighing 1.4 to 3.0 g dinitolmide (Shanghai Anpu Scientific Instrument Co., Ltd., Cat. No.: 148-01-6) and dissolving in 200 to 500 ml anhydrous ethanol, adding 3.5 to 5.0 g 10% Palladium Carbon (Pd/C) to perform a catalytic hydrogenation at 20 to 60° C. for 12 to 30 hours, filtering to remove the solvent, and separating 5-amino nitolmide after column chromatography (silica gel, 120 to 200 meshes) (elution solution: dichloromethane/methanol, 20:1 (v/v));

Weighing 0.4 to 1.0 g 5-amino nitolmide, 0.3 to 0.5 g succinic anhydride and 1 ml pyridine and dissolving in 10 to 20 ml DMSO, reacting under stirring at 20 to 60° C. for 10 to 24 hours, removing the solvent through evaporation, and performing recrystallization in ethanol-water system after column chromatography (silica gel, 120 to 200 meshes) (elution solution: dichloromethane/methanol, 20:1 (v/v)) to produce 5-amino nitolmide mono-succinamide (i.e., the dinitolmide hapten).

b. The Synthesis of the Immunogen

The immunogen was prepared by coupling the resultant dinitolmide hapten to bovine serum albumin (BSA) via carbodiimide method (see Yang Liguo, Hu Shaochang, Wei Pinghua, et al. (Ed.) "Enzyme Immunoassay Technology", Nanjing University Press, pages 254 to 255).

The particular procedures are as follows:

Weighing 8 mg dinitolmide hapten and dissolving in 1 mL N,N-dimethyl formamide (DMF), adding 6 mg carbodiimide/N-hydroxyl succinimide (EDC/NHS) dissolved in 0.2 mL of 0.1 mol/L 2-morpholino ethanesulfonic acid (MES), reacting at room temperature for 15 min, adding 30 mg bovine serum albumin dissolved in 1.8 mL 0.1 mol/L phosphate buffer solution and reacting for 16 hours, performing dialysis against 0.01 mol/L phosphate buffer for 3 days with three times of solution exchange every day to produce the immunogen.

c. The Synthesis of the Coating Antigen

The coating antigen was prepared by coupling the dinitolmide hapten to ovalbumin (purchased from Shanghai Seebio Biotech, Inc.) via carbodiimide method.

The particular procedures are as follows:

Dissolving 5 mg dinitolmide hapten in 1 mL DMF, adding 6 mg EDC/NHS dissolved in 0.2 mL of 0.1 mol/L MES and reacting at room temperature for 15 min, adding 30 mg ovalbumin dissolved in 1.8 mL 0.1 mol/L PBS and reacting for 16 hours, performing dialysis against 0.01 mol/L PBS for 3 days with three times of solution exchange every day to produce the coating antigen.

2. The Preparation of Monoclonal Antibody a. Animal Immunization 6 to 8 week old healthy Balb/c mice (purchased from the Academy of Military Medical Science of the Chinese People's Liberation Army) were immunized via subcutaneous multiple site injection with an immunization dose of 150 µg per mouse. The immunogen was homogeneously mixed with equal volume of complete Freund's adjuvant (purchased from Sigma, Cat. No. F5881) for the first immunization, and with equal volume of incomplete Freund's adjuvant (purchased from Sigma, Cat. No. F5506) for the subsequent immunizations.

b. Cell Fusion and Cloning

When the assay result of mice serum was high, its spleen cells were removed and fused with SP2/0 myeloma cells (purchased from Institute of Genetics and Developmental Biology, Chinese Academy of Science) in a ratio of 9:1 (the amount ratio). The supernatant of the cells was assayed via indirect competitive ELISA, and the positive wells were screened. The positive wells were cloned with a limited dilution method until the hydridoma cell lines secreting monoclonal antibody are obtained.

After screening, dinitolmide murine monoclonal hybridoma cell line E-2-4 was obtained. This hybridoma cell line was deposited in China General Microbiological Culture Collection Center (CGMCC, Institute of Microbiology, Chinese Academy of Sciences, No 1 West Beichen Road, Chaoyang, District, Beijing 100101, China) under the accession number of CGMCC No. 6143 on May 21, 2012. The antibody secreted by said hybridoma cell line had a good specificity to dinitolmide and its sensitivity is up to 1 µg/L. The affinity constant of the monoclonal antibody was about $1.8 \times 10^6 M^{-1}$ as determined by ELISA.

c. Cryopreservation and Recovery of the Cells

The dinitolmide monoclonal hybridoma cell line E-2-4 was prepared into a cell suspension having a density of $1 \times 10^6$ cells/mL with a cryopreservation solution, and preserved in liquid nitrogen for a long term. For recovery, the cryopreservation tube was removed and immediately placed in water bath at 37° C. for quick thawing. After the cryopreservation solution was removed through centrifugation, the cells were transferred into a culture bottle for cultivation.

d. The Production and Purification of the Monoclonal Antibody

Several 6 to 8 week old Balb/c mice were intraperitoneally injected with sterile paraffin oil, 0.5 mL/mouse. After 7 days, up to $5 \times 10^7$ cells of the dinitolmide monoclonal hybridoma cell line E-2-4 were intraperitoneally injected to each mouse, and the ascites were collected 7 days later. The ascites were purified via octanoic acid-saturated ammonium sulfate method, and the product was preserved at −20° C.

3. The Preparation of the Polyclonal Antibody

The New Zealand white rabbits (purchased from Xinglong Experimental Animal Breeding Plant, Haidian District, Beijing) were used as the animals to be immunized. The conjugate of the dinitolmide hapten and bovine serum albumin was used as the immunogen. And the dose for immunization was 1.5 mg/kg. For the first immunization, the immunogen was mixed with equal volume of complete Freund's adjuvant (supra) to prepare an emulsifying agent, and the emulsifying agent was subcutaneously injected at multiple sites on neck and back portion. The same dose of immunogen was emulsified by mixing with equal volume of incomplete Freund's adjuvant (supra) and used for a booster immunization at an interval of 3 to 4 weeks. The rabbits were immunized 5 times in total, and for the final immunization, no adjuvant was added. The blood was collected 10 days after the final immunization, and the serum antibody titer was determined. The blood was collected from heart, and the polyclonal antibody was purified via octanoic acid-saturated ammonium sulfate method (Chen Dan, Sun Guangrui, Liu Zengshan, The application of octanoic acid-ammonium sulfate precipitation method in the purification of monoclonal antibody [J] Anhui Agricultural Sciences, 2007, 35 (26): 8105-8108).

4. The Process for the Preparation of Goat Anti-Mouse Secondary Antibody:

The goats (purchased from Beijing Xinglong Experimental Animal Breeding Plant) were used as the animals to be immunized. Pathogen free goats were immunized with mice derived antibody as the immunogen to produce the goat anti-mouse secondary antibody.

The preparation of goat anti-rabbit secondary antibody: the goats were used as the animals to be immunized. Pathogen free goats were immunized with rabbit derived antibody to produce the goat anti-rabbit secondary antibody.

5. The Preparation of the Microtiter Plates

The dinitolmide-conjugated antigen was diluted to 0.05 to 0.2 µg/ml with a coating buffer. 100 µl was added to each well, and the plate was cultured at 37° C. for 2 hours or at 4° C. overnight. The coating buffer was poured, and the plate was washed 2 times with 20-fold deionized water-diluted concentrated washing solution. The liquid in the wells was poured. After the residual moisture was absorbed with absorbent paper, 150 to 200 µl blocking solution was added to each well, and the plate was cultured at 37° C. for 2 hours. The liquid in the wells was poured. The plate was sealed with aluminum film in vacuum after it was dried, and preserved in a dry place at 4° C. for future use.

The coating solution is 0.1 to 0.2 mol/L carbonic acid buffer, pH 9.1-9.6. The blocking solution is 0.02 to 0.05 mol/L phosphate buffer containing 5-10 wt % calf serum and 0.05 wt % sodium azide, pH 7.1 to 7.4.

6. The Preparation of Enzyme-Labeled Goat Anti-Mouse Secondary Antibody

The horseradish peroxidase (HRP) was conjugated to the secondary antibody via a modified sodium periodate method. In the classical sodium periodate method, the ratio of the molar concentration of the enzyme to that of the secondary antibody in the reaction system should be 4:1. Since the horseradish peroxidase will generate many sites for binding to the secondary antibody under a strong oxidation, such activated horseradish peroxidase molecule may serve as the bridge for connecting each molecule, and thus, the enzymatic activity of the enzyme conjugate is reduced, and many polymers are comprised in the resultant conjugate. In order to solve this problem, the inventor has made a modification to the classical method. That is, the process for blocking amino groups is omitted, because there are actually few of amino groups which are capable of generating self amino-linkage.

The ratio of the molar concentration of horseradish peroxidase to that of the secondary antibody is reduced to 2:1. As compared with the classical method, the modified method is simpler, and the loss of the enzyme activity is reduced.

IV. The Residual Dinitolmide in the Sample is Detected with the Kit as Described Above 1. Sample Preparation a) The Chicken Tissues (Chicken Meat and Chicken Liver)

Weighing and adding 1.0±0.05 g homogeneous sample of the above mentioned tissues to a 50 mL polystyrene centrifuge tube, adding 8 mL acetonitrile and shaking for 10 min; centrifuging at a speed of 3000 g or more at room temperature for 5 min; transferring 2 mL upper liquid to a 10 mL clean glass test tube, and drying in a 50 to 60° C. water bath under nitrogen flow; adding 1 mL n-hexane and performing vortex for 30 seconds to dissolve the dried residual product; adding 1 mL extraction solution and performing vortex for 30 seconds, and centrifuging at a speed of 3000 g or more at room temperature for 5 min; and collecting 50 µl bottom liquid for analysis.

b) Feed Samples

Weighing and adding 1.0±0.05 g homogeneous sample of the above mentioned feed samples to a 50 mL polystyrene centrifuge tube, adding 8 mL acetonitrile and shaking for 10 min; centrifuging at a speed of 3000 g or more at room temperature for 5 min; transferring 1 mL upper liquid to a 10 mL clean glass test tube, and drying in a 50 to 60° C. water bath under nitrogen flow; adding 1 mL n-hexane and performing vortex for 30 seconds, and adding 1 mL extraction solution and performing vortex for 30 seconds; centrifuging at a speed of 3000 g or more at room temperature for 5 min; and collecting 50 µl bottom liquid for analysis.

2. Detection

50 µl dinitolmide standard solution or sample solution was added to the micro-wells of the microtiter plate coated with dinitolmide-conjugated antigen. And 50 µl dinitolmide monoclonal antibody working solution with a titer of 1:2×10$^5$ was also added to the micro-wells. The plate was covered with a plate-covering film, and was placed in a constant temperature incubator at 25° C. for reaction for 30 min. The liquid in the wells was poured. 250 µl 0.01 to 0.02 mol/L washing solution was added to the wells, and the liquid in the wells was poured after 30 seconds. The plate was washed 5 times in total by repeating the above manipulation. Finally, the residual moisture was absorbed with absorbent paper. 100 µl working solution of the horseradish peroxidase labeled goat anti-mouse secondary antibody with a titer of 1000 was added, and the plate was placed in a constant temperature incubator at 25° C. for reaction for 30 min. The liquid in the wells was poured out, and the step of washing the plate was repeated. In each well, 50 µl substrate solution A, urea hydrogen peroxide, was added, and 50 µl substrate solution B, tetramethylbenzidine (TMB), was added. The substrate solutions were mixed uniformly under gentle shaking. The plate was developed in a constant temperature incubator at 25° C. in dark for 15 min. 50 µl 2 mol/L hydrochloric acid stop solution was added to each well and was mixed uniformly under gentle shaking. The absorbance ($OD_{450}$) of each well was determined in Microplate Reader (Thermo Scientific, model MK3) at a wave length set to 450 nm.

3. Analysis of the Detection Results

The average (B) of the absorbance values of standard solutions at each concentration as obtained above is divided by the absorbance value ($B_0$) of the first standard solution (0 standard) and then is multiplied by 100%, to get the percent absorbance value.

$$\text{Percent absorbance value } (\%) = \frac{B}{B_0} \times 100\%$$

In the above formula, B represents the average absorbance value of the standard solutions or sample solutions, and $B_0$ represents the average absorbance value of the 0 µg/L standard solution.

Figure 2:
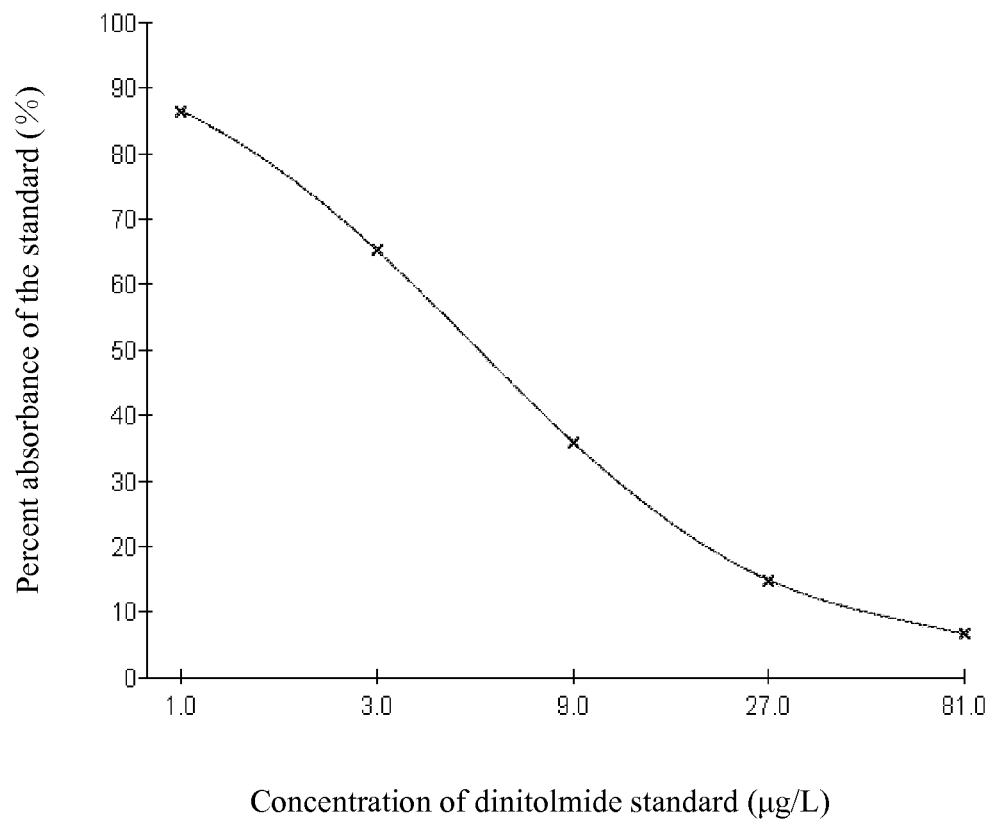
FIG. 2 is the standard curve plot of the kit comprising the conjugate of dinitolmide hapten and carrier protein as the coating antigen.

The concentration of the dinitolmide standard (µg/L) was plotted on X-axis, and the percent absorbance value was plotted on Y-axis, and thus, a standard curve was plotted (FIG. 2). The percent absorbance value of sample solutions is calculated by the same method. The residual amount of dinitolmide in the sample will be read from the standard curve according to the concentration of each sample. Further, the results of the detection in the present invention may be analyzed with the method of regression equation, and then the concentration of the sample solution is calculated. Determination of the Precision, Accuracy, Detection Limits and Stability Indexes of the Kit Prepared with the Monoclonal Antibody The kit of the present invention has a detection sensitivity of 0.1 µg/L for dinitolmide, with accuracy of 80%-100% and a precision of less than 15%.

As compared with the chromatography, the kit of the present invention has the following advantages: as for the chromatography, the instrument is expensive, it has high requirements for the technique, and the sample should be subjected to purification treatment, so it is not suitable for on-site screening. However, the enzyme-linked immunosorbent assay technique is capable of qualitatively and quantitatively measuring the residual noxious substance in trace amount and has low requirements for the instrument, the cost of the detection is low, its manipulation is rapid and simple, the process of the preparation of the sample is simple, its requirements for the professional skills of the technician are low, and it has a high sensitivity, so, it can be applied for the on-site rapid detection of a large number of samples.

1. Precision Test of the Standard

A batch of microtiter plates was randomly selected from those manufactured during 3 different time periods, respectively. Ten kits were randomly selected from each batch, and twenty micro-wells were randomly selected from each plate. The absorbance value of 9 µg/L standard solution was measured, and the coefficient of variation was calculated.

TABLE 1

Standard repeatability test (CV %)

|      |          | 1   | 2   | 3   | 4   | 5   | 6   | 7   | 8   | 9   | 10  |
|------|----------|-----|-----|-----|-----|-----|-----|-----|-----|-----|-----|
| CV % | 01 batch | 4.5 | 6.4 | 5.8 | 7.9 | 4.5 | 6.3 | 9.2 | 4.3 | 5.0 | 6.5 |
|      | 02 batch | 7.2 | 2.3 | 4.2 | 5.7 | 6.3 | 4.0 | 8.2 | 6.0 | 7.8 | 4.1 |
|      | 03 batch | 5.3 | 4.8 | 6.5 | 5.5 | 8.3 | 4.9 | 6.0 | 7.4 | 7.7 | 8.3 |

It was concluded from the above testing results that the coefficient of variation of 10 tests of standard for each batch of kits was between 2.3% and 9.2%, in line with the prescription that the precision is less than or equal to 25%.

2. The Precision and Accuracy Test of Samples

Accuracy refers to the degree of compliance between the measured value and the true value. In ELISA, the accuracy of the kit is generally expressed as the percent recovery, and the precision is generally expressed as the coefficient of variation. According to the extraction method of the kit, the dinitolmide solutions at two concentrations, 40 µg/kg and 80 µg/kg were added to the blank feed samples and dinitolmide was recovered; and the dinitolmide solutions at two concentrations, 10 µg/kg and 20 µg/kg, were added to the blank chicken meat and chicken liver samples and dinitolmide was recovered. Quadruplication was performed for each sample at each concentration. And the coefficient of variation was calculated. The testing results were shown in Table 2 and Table 3.

TABLE 2

The accuracy and precision of the feed samples with dinitolmide addition (µg/kg)

| Sample | Addition concentration (µg/kg) | Percent recovery (n = 4)% | Intra-batch coefficient of variation (n = 4)% | Inter-batch coefficient of variation (n = 3)% |
|--------|-------------------------------|---------------------------|-----------------------------------------------|-----------------------------------------------|
| Feed   | 40                            | 86.9                      | 8.6                                           | 11.5                                          |
|        | 80                            | 92.5                      | 10.2                                          | 13.4                                          |

TABLE 3

The accuracy and precision of the chicken meat and chicken liver samples with dinitolmide addition (µg/kg)

| Sample        | Addition concentration (µg/kg) | Percent recovery (n = 4)% | Intra-batch coefficient of variation (n = 4)% | Inter-batch coefficient of variation (n = 3)% |
|---------------|-------------------------------|---------------------------|-----------------------------------------------|-----------------------------------------------|
| Chicken meat  | 10                            | 85.6                      | 11.5                                          | 13.0                                          |
|               | 20                            | 80.1                      | 9.6                                           | 10.5                                          |
| Chicken liver | 10                            | 80.3                      | 12.3                                          | 13.7                                          |
|               | 20                            | 89.7                      | 11.4                                          | 14.5                                          |

As known from Table 2, the average percent recovery of the feed samples with addition of dinitolmide at two concentrations, 40 µg/kg and 80 µg/kg, was in a range of from 86.9% to 92.5%, the intra-batch coefficient of variation was in a range of from 8.6 to 10.2%, and the inter-batch coefficient of variation was in a range of from 11.5% to 13.4%.

From Table 3, the average percent recovery of the chicken meat and chicken liver samples with addition of dinitolmide at two concentrations, 10 µg/kg and 20 µg/kg, was in a range of from 80.1% to 89.7%, the intra-batch coefficient of variation was in a range of from 9.6 to 12.3%, and the inter-batch coefficient of variation was in a range of from 10.5% to 14.5%.

The above testing results satisfied with the precision and accuracy criteria of the recorded reference evaluation criteria of kit, documented in Ministry of Agriculture [2005] No. 17, Annex 2.

3. The Detection Sensitivity of the Kit

The negative samples without dinitolmide were measured twenty times with the kit. The lowest detection limit of the kit was expressed as the average value of the measured results plus three folds of the standard deviation.

The results were shown in the following table, indicating that the lowest detection limit of the kit was 0.95 µg/kg.

TABLE 4

Statistics of the measurement results of negative samples (µg/kg)

| | Sample No. | | | | | | | |
|---|---|---|---|---|---|---|---|---|
| | 1 | 2 | 3 | 4 | 5 | 6 | 7 | 8 |
| Measured value | 0.30 | 0.00 | 0.00 | 0.34 | 0.48 | 0.40 | 0.25 | 0.00 |

| | Sample No. | | | | | | | |
|---|---|---|---|---|---|---|---|---|
| | 9 | 10 | 11 | 12 | 13 | 14 | 15 | 16 |
| Measured value | 0.35 | 0.38 | 0.20 | 0.61 | 0.00 | 0.61 | 0.00 | 0.33 |

| | Sample No. | | | | Average | S.D. | Lowest detection limit |
|---|---|---|---|---|---|---|---|
| | 17 | 18 | 19 | 20 | | | |
| Measured value | 0.00 | 0.42 | 0.63 | 0.00 | 0.27 | 0.23 | 0.95 |

4. Stability Test of the Kit

The condition for the preservation of the kit is 2 to 8° C. The kit was tested after 12 months of storage, and the maximum absorbance value (0 standard) and 50% inhibition concentration of the kit, and the actually measured values after adding dinitolmide were within the normal range. Taking into consideration that abnormal storage conditions would occur during the transportation and application, an accelerated aging test was performed by keeping the kit at a storage condition of 37° C. for 6 days. The testing result indicated that all the indexes of the kit were in full compliance with the requirements. In addition, considering that the kit might be frozen, the kit was kept at −20° C. in a refrigerator for 5 days. And, the testing result also indicated that all the indexes of the kit were normal. From the above results, it can be concluded that the kit can be stored at 2 to 8° C. for 12 months or more.

Determination of the Precision, Accuracy, Detection Limits and Stability Indexes of the Kit Prepared with the Polyclonal Antibody The same method of determining the precision, accuracy, detection limits and stability indexes of the kit prepared with the monoclonal antibody was used. After determination, the polyclonal antibody kit as prepared with the above method had a precision between 6.9% and 14.2%, with an accuracy from 60% to 100%, and a detection sensitivity of 3.67 µg/kg. The kit can be stored at 2~8° C. for 12 months or more.

Example 2 The Kit Comprising Dinitolmide Antibody as the Coating Antigen (1) a microtiter plate coated with the coating antigen (the coating antigen is dinitolmide antibody);

(2) enzyme-labeled dinitolmide hapten: horseradish peroxidase labeled dinitolmide hapten;

(3) dinitolmide standard solution series: six vials of solution having the concentration of 0 μg/L, 1 μg/L, 3 μg/L, 9 μg/L, 27 μg/L, and 81 μg/L, respectively;

(4) substrate solution which consists of substrate solution A and substrate solution B, wherein the substrate solution A is urea hydrogen peroxide or hydrogen peroxide, and the substrate solution B is tetramethyl benzidine or o-phenylene diamine;

(5) stop solution, which is 0.5 to 2 mol/L hydrochloric acid or sulfuric acid;

(6) concentrated washing solution, which is 0.2 to 0.4 mol/L phosphate buffer comprising 0.2 to 1.0 wt % Tween-20 and 0.01 to 0.06 wt % sodium azide, pH 7.1-7.6; and (7) a concentrated extraction solution, which is 0.1 to 0.2 mol/L phosphate buffer, pH 7.2-7.8.

Example 3 The Kit Comprising Secondary Antibody as the Coating Antigen (1) a microtiter plate coated with the coating antigen (the coating antigen is secondary antibody);

(2) dinitolmide monoclonal antibody working solution or dinitolmide polyclonal antibody working solution;

(3) enzyme-labeled dinitolmide hapten: horseradish peroxidase labeled dinitolmide hapten;

(4) dinitolmide standard solution series: six vials of solution having the concentration of 0 μg/L, 1 μg/L, 3 μg/L, 9 μg/L, 27 μg/L, and 81 μg/L, respectively;

(5) substrate solution which consists of substrate solution A and substrate solution B, wherein the substrate solution A is urea hydrogen peroxide or hydrogen peroxide, and the substrate solution B is tetramethyl benzidine or o-phenylene diamine;

(6) stop solution, which is 0.5 to 2 mol/L hydrochloric acid or sulfuric acid;

(7) concentrated washing solution, which is 0.2 to 0.4 mol/L phosphate buffer comprising 0.2 to 1.0 wt % Tween-20 and 0.01 to 0.06 wt % sodium azide, pH 7.1-7.6; and (8) a concentrated extraction solution, which is 0.1 to 0.2 mol/L phosphate buffer, pH 7.2-7.8.

Example 4 The Kit Comprising the Conjugate of Dinitolmide Hapten and Carrier Protein as the Coating Antigen (1) a microtiter plate coated with the coating antigen (the coating antigen is the conjugate of dinitolmide hapten and carrier protein);

(2) enzyme-labeled antibody working solution: horseradish peroxidase labeled dinitolmide monoclonal antibody or horseradish peroxidase labeled dinitolmide polyclonal antibody;

(3) dinitolmide standard solution series: six vials of solution having the concentration of 0 μg/L, 1 μg/L, 3 μg/L, 9 μg/L, 27 μg/L, and 81 μg/L, respectively;

(4) substrate solution which consists of substrate solution A and substrate solution B, wherein the substrate solution A is urea hydrogen peroxide or hydrogen peroxide, and the substrate solution B is tetramethyl benzidine or o-phenylene diamine;

(5) stop solution, which is 0.5 to 2 mol/L hydrochloric acid or sulfuric acid;

(6) concentrated washing solution, which is 0.2 to 0.4 mol/L phosphate buffer comprising 0.2 to 1.0 wt % Tween-20 and 0.01 to 0.06 wt % sodium azide, pH 7.1-7.6; and (7) a concentrated extraction solution, which is 0.1 to 0.2 mol/L phosphate buffer, pH 7.2-7.8.

The invention claimed is:

1. An enzyme-linked immunosorbent assay kit for detecting dinitolmide, comprising:
   (i) dinitolmide antibody, wherein the dinitolmide antibody is a dinitolmide monoclonal antibody or dinitolmide polyclonal antibody;
   coating antigen, wherein the coating antigen is a conjugate of dinitolmide hapten and carrier protein; and
   enzyme conjugate, wherein the enzyme conjugate is an enzyme-labeled secondary antibody;
   (ii) coating antigen, wherein the coating antigen is a dinitolmide monoclonal antibody or dinitolmide polyclonal antibody; and
   enzyme-labeled dinitolmide hapten;
   (iii) dinitolmide antibody, wherein the dinitolmide antibody is a dinitolmide monoclonal antibody or dinitolmide polyclonal antibody;
   coating antigen, wherein the coating antigen is a secondary antibody; and
   enzyme-labeled dinitolmide hapten; or
   (iv) dinitolmide antibody, wherein the dinitolmide antibody is an enzyme-labeled dinitolmide monoclonal antibody or dinitolmide polyclonal antibody; and
   coating antigen, wherein the coating antigen is a conjugate of dinitolmide hapten and carrier protein;
   wherein the dinitolmide hapten in (i)-(iv) is 5-amino nitolmide mono-succinamide.

2. The enzyme-linked immunosorbent assay kit according to claim 1, wherein the carrier protein is thyroid protein, bovine serum protein, mouse serum protein, rabbit serum protein, human serum protein, hemocyanin, fibrinogen or ovalbumin.

3. The enzyme-linked immunosorbent assay kit according to claim 1, wherein the kit further comprises dinitolmide standard solution series, substrate solution, concentrated washing solution, stop solution and/or concentrated extraction solution;
   the concentrated washing solution is 0.2 to 0.4 mol/L phosphate buffer comprising 0.2 to 1.0 wt % Tween-20 and 0.01 to 0.06 wt % sodium azide, pH 7.1-7.6;
   the concentrated extraction solution is 0.1 to 0.2 mol/L phosphate buffer, pH 7.2-7.8;
   the substrate solution consists of substrate A and substrate B, wherein the substrate solution A is hydrogen peroxide or urea hydrogen peroxide, and the substrate solution B is o-phenylene diamine or tetramethyl benzidine; and
   the stop solution is 0.5 to 2 mol/L sulfuric acid or hydrochloric acid solution.

4. The enzyme-linked immunosorbent assay kit according to claim 1, wherein the dinitolmide hapten is prepared by the method comprising the following steps: catalytically (e.g., Pd/C) hydrogenating dinitolmide to produce a mono-amine derivative, and then reacting the mono-amine derivative with succinic anhydride to produce the dinitolmide hapten.

5. The enzyme-linked immunosorbent assay kit according to claim 1, wherein the dinitolmide antibody is prepared by using the conjugate of the dinitolmide hapten and carrier protein as immunogen.

6. The enzyme-linked immunosorbent assay kit according to claim 1, wherein the enzyme-labeled secondary antibody is prepared by coupling the enzyme conjugate to the secondary antibody via sodium periodate method.

7. The enzyme-linked immunosorbent assay kit according to claim 1, wherein the dinitolmide monoclonal antibody is secreted by a murine hybridoma cell line E-2-4 under the accession number of CGMCC No. 6143.

8. A method for detecting dinitolmide in a sample, comprising the following steps:
   1) sample preparation: a homogeneous specimen of the sample is weighed and added to a centrifuge tube, centrifuged after extracting with acetonitrile; the supernatant is removed and blow-dried in a water bath; the residue is dissolved by adding n-hexane, and the impurity is removed; the solution is extracted with extraction solution, and the bottom solution after centrifugation is used for analysis, wherein the extraction solution is 0.025 to 0.05 mol/L phosphate buffer, pH 7.2 to 7.8;
   2) quantitatively and/or qualitatively measuring dinitolmide in the bottom solution of step 1) using the enzyme-linked immunosorbent assay kit according to claim 1.

9. The method according to claim 8, wherein the sample is animal feed or animal tissue sample.

10. A murine hybridoma cell line E-2-4 under the accession number of CGMCC No. 6143.

11. The enzyme-linked immunosorbent assay kit according to claim 2, wherein the dinitolmide monoclonal antibody is secreted by a murine hybridoma cell line E-2-4 under the accession number of CGMCC No. 6143.

12. The enzyme-linked immunosorbent assay kit according to claim 3, wherein the dinitolmide monoclonal antibody is secreted by a murine hybridoma cell line E-2-4 under the accession number of CGMCC No. 6143.

13. The enzyme-linked immunosorbent assay kit according to claim 4, wherein the dinitolmide monoclonal antibody is secreted by a murine hybridoma cell line E-2-4 under the accession number of CGMCC No. 6143.

14. The enzyme-linked immunosorbent assay kit according to claim 5, wherein the dinitolmide monoclonal antibody is secreted by a murine hybridoma cell line E-2-4 under the accession number of CGMCC No. 6143.

15. The enzyme-linked immunosorbent assay kit according to claim 6, wherein the dinitolmide monoclonal antibody is secreted by a murine hybridoma cell line E-2-4 under the accession number of CGMCC No. 6143.

16. The enzyme-linked immunosorbent assay kit according to claim 1, wherein the secondary antibody is a goat anti-mouse secondary antibody or goat anti-rabbit secondary antibody.

17. The enzyme-linked immunosorbent assay kit according to claim 5, wherein the conjugate is formed by coupling the dinitolmide hapten to the carrier protein via carbodiimide method.

18. The method according to claim 9, wherein the sample is chicken feed, chicken meat or chicken liver.

* * * * *